United States Patent
Hoogenraad et al.

(10) Patent No.: US 6,327,489 B1
(45) Date of Patent: Dec. 4, 2001

(54) METHOD OF LOCALIZING AN OBJECT IN A TURBID MEDIUM

(75) Inventors: Johannes H. Hoogenraad, Veldhoven; Gert W. 'T Hooft, Eindhoven, both of (NL)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/486,158
(22) PCT Filed: Jun. 22, 1999
(86) PCT No.: PCT/IB99/01165
§ 371 Date: Feb. 22, 2000
§ 102(e) Date: Feb. 22, 2000
(87) PCT Pub. No.: WO99/66832
PCT Pub. Date: Dec. 29, 1999

(30) Foreign Application Priority Data

Jun. 25, 1998 (EP) .................................................. 98202109

(51) Int. Cl.$^7$ ....................................................... A61B 5/00
(52) U.S. Cl. .......................... 600/407; 600/473; 600/476; 250/341.1; 250/358.1; 356/432
(58) Field of Search ........................... 600/473, 475–479, 600/310, 407; 356/300, 337, 338, 343, 446; 250/330, 338.1, 340, 341.1, 358.1; 382/128

(56) References Cited

U.S. PATENT DOCUMENTS

| | | | |
|---|---|---|---|
| 5,137,355 | * 8/1992 | Barbour et al. | 600/475 |
| 5,402,338 | * 3/1995 | Ito | 600/407 |
| 5,625,458 | * 4/1997 | Alfano et al. | 356/446 |
| 5,694,938 | * 12/1997 | Feng et al. | 600/475 |
| 6,083,172 | * 7/2000 | Baker, Jr. et al. | 600/500 |

OTHER PUBLICATIONS

"The Forward and Inverse Problems in Time Resolved Infra–Red Imaging" by Simon R. Arridge in SPIE, IS11:35, 1993.

"Fundamentals of Image Processing" by A.K. Jain et al., Prentica Hall, 1989, pp. 439–441.

* cited by examiner

Primary Examiner—Ruth S. Smith
(74) Attorney, Agent, or Firm—John F. Vodopia

(57) ABSTRACT

The invention relates to a method of localizing an object in a turbid medium. After measurement of the intensities for a plurality of light paths between the light sources and the detectors, the measured intensities are normalized. Subsequently, an image of the interior of the turbid medium is reconstructed on the basis of the measured intensities. In order to counteract artefacts in the reconstructed image, the combination includes a weighting factor which reduces the effect exerted on the reconstructed image by the measured intensities with a high noise factor in comparison with the effect exerted thereon by the measured intensities with a low noise factor.

6 Claims, 2 Drawing Sheets

METHOD OF LOCALIZING AN OBJECT IN A TURBID MEDIUM

BACKGROUND OF THE INVENTION

1. Field of the Invention

The invention relates to a method of localizing an object in a turbid medium, which method includes the following steps:

irradiation of the turbid medium, measurement of intensities of a part of the light transported through the turbid medium along a plurality of light paths from a source point where the light enters the turbid medium to a measuring point where the light leaves the turbid medium, reconstruction of an image of the interior of the turbid medium from a combination of the measured intensities.

The invention also relates to a device for localizing objects in turbid media, which device includes:

a light source for irradiating the turbid medium, means for coupling the light to be generated from the light source into the turbid medium at different angles, a photodetector for converting the light transported through the turbid medium into a photodetector signal, means for converting the photodetector signal in measured intensities, and a control unit for reconstructing an image of the interior of the turbid medium from the measured intensities.

2. Description of Related Art

In the context of the present application the term light is to be understood to mean electromagnetic radiation of a wavelength in the range of from 400 to 1400 nm. Furthermore, a turbid medium is to be understood to mean a substance consisting of a material having a high light scattering coefficient. Examples in this respect are an Intralipid solution or biological tissue.

A method of this kind is known from the article "The forward and inverse problems in time resolved infra-red imaging", by S. R. Arridge, SPIE, IS11:35, 1993. The known method can be used for in vivo breast examinations. to determine the presence of tumors in breast tissue of a human or animal female. According to the known method the turbid medium is irradiated from different positions, intensities of light transported through the turbid medium being measured for one irradiation position in different positions where the light leaves the turbid medium. The known algebraic reconstruction technique constitutes an iterative method in which per iteration step a next image is determined in dependence on a sensitivity matrix and an intensity measurement and a previously determined image which, after the first iteration, is chosen to be equal to the image determined during the previous iteration step. Herein, a sensitivity matrix is to be understood to mean a matrix in which a matrix element (i, j) contains a sensitivity function, the row number (i) of the matrix element corresponding to a light source and a measuring position of an intensity measurement i whereas the column number (j) of the matrix element corresponds to a position in space of a volume element j. The sensitivity function of a matrix element A(i,j) is given by the formule:

$$F(s(i), d(i), \kappa) = \frac{V\kappa_0}{2\pi} \frac{|s(i)-d(i)|}{|s(i)-p(j)| \times |p(j)-d(i)|} e^{-\kappa_0(|s(i)-p(j)|+|p(j)-d(i)|-|s(i)-d(i)|)} \quad (1)$$

in which

V represents the volume of a volume element j in the turbid medium, s(i)–d(i) represents a distance between a light source in a position s(i) and a measuring position d(i) for a measurement (i), s(i)–po) represents a distance between the position of the light source s(i) during the measurement (i) and the position p(j) of a volume element (j) for which the variation of the attenuation coefficient κ is determined, p(j)–d(i) represents the distance between the position of said volume element j and the measuring position d(i) during the measurement (i), and F(s(i),d(i),κ) represents the relative variation of the measured intensity in a position d(i) of a light source in a position s(i).

Furthermore, an attenuation coefficient is to be understood to mean the inverse diffuse absorption distance κ, given by the formula $$\kappa = \sqrt{3\mu_a \mu'_s},$$

in which $\mu'_s$ is the inverse transport-corrected free path length, and $\mu_a$ represents the absorption coefficient.

It is a drawback of the known method that the image suffers from artefacts in the form of stripes which correspond to a path from a first position where light enters the turbid medium to a second position where light leaving the turbid medium has been measured. Furthermore, artefacts in the form of a more or less regular structure occur at the center of the image.

Citation of a reference herein, or throughout this specification, is not to be construed as an admission the such reference is prior art to the Applicants' invention of the invention subsequently claimed.

SUMMARY OF THE INVENTION

It is an object of the invention to counteract said artefacts in the image. To achieve this, the method according to the invention is characterized in that the combination contains a weighting factor which reduces an effect exerted on the reconstructed image by the measured intensities with a high noise factor relative to the effect exerted thereon by the measured intensities with a low noise factor. The invention is based on the recognition of the fact that the density of possible light paths near the edge of the turbid medium is higher than the density of possible light paths at the center of the turbid medium, because long as well as short light paths extend through a volume element near the edge of the turbid medium whereas only long light paths extend through a volume element at the center of the turbid medium. Furthermore, the measured intensities of light having traveled along a long light path through the turbid medium are generally lower than the measured intensities of light having traveled along a short light path through the turbid medium. Due to both factors, the effect of noise on a reconstruction of the center of the image is greater than that on the reconstruction of the edges of the image. In order to counteract the effects of noise, for example corrections can be applied in which intensities which are less than 10 times an absolute value of the noise in the intensity measurement itself are excluded from the reconstruction. However, when a weighting factor having a value 1 or 0 is chosen, it may occur that subsequent to the reconstruction the center of the image contains an area for which it may be impossible to determine a value because no measurements are available for the relevant area. Furthermore, this area may become ragged and may contain extreme values because only few measurements are available for reconstruction in comparison with the remainder of the image. On the basis of, for example an absolute measured intensity and an absolute measured intensity of a reference measurement, a weighting factor can be assigned to each intensity measured, the weighting factor being in a range from the value 0 to the value 1. Because all known reconstruction techniques, such as said algebraic reconstruction technique or back-transformation, assign location-dependent weights to the measured intensities, analogously a weighting factor is introduced in the reconstruction.

A special version of the method according to the invention is characterized in that for a light source and a measuring position in which an intensity is measured the method also includes the following steps:

determination of estimated intensities from a transformation of a predetermined first image, determination of a difference between the measured intensities and the estimated intensities, and determination of a next image from the first image, a convergence factor and a back-transformation of the difference, the convergence factor being chosen to be depending on the weighting factor. These steps are repeated for all light sources and measuring positions. The convergence factor can be chosen equal to a constant times the weighting factor. As a result of the introduction of a convergence factor equal to the weighting factor, in the algebraic reconstruction technique a change of the next image relative to the first image is influenced less by a measurement containing a large amount of noise than the change in the next image which is due to a measurement involving little noise.

A further version of the method according to the invention is characterized in that the transformation contains a product of a sensitivity matrix and the first image.

A further version of the method according to the invention is characterized in that the back-transformation contains a product of an estimate of an inverse sensitivity matrix and the difference between the measured intensities and the calculated intensities. An example of an estimate of the inverse sensitivity matrix is the transposed sensitivity matrix normalized per row.

A further version of the method according to the invention is characterized in that the method also includes the following steps:

determination of variations of the attenuation coefficients of the light paths from the measured intensities, and determination of a variation of the attenuation coefficient of a volume element of the turbid medium by means of a back-transformation which contains a weighted mean value of an estimate of the inverse sensitivity matrix with the variations determined for the attenuation coefficients of the light paths, the effect of the noise factor on the reconstruction being determined by the product of the weighting factor and the elements of the estimate of the inverse sensitivity matrix. The transposed sensitivity matrix constitutes an example of an estimate of the inverse sensitivity matrix. The product of the weighting factor and the elements of the transposed sensitivity matrix makes it possible that the intensities measured with a high noise factor exert a small effect only on the reconstruction in comparison with measurements with a low noise factor.

A further version of the method according to the invention is characterized in that the weighting factor is dependent on a reciprocal value of a noise factor. As a result of this step it is achieved that the weighting factor is small in the case of low quality measurements and that the weighting factor is large for high quality measurements.

A further version of the method according to the invention is characterized in that the measured intensities are corrected by way of a normalized intensity which is determined by a combination of the measured intensity associated with a light path and a measured reference intensity associated with the light path in a reference medium. Because the reconstruction does not utilize the absolute measured intensity but a normalized intensity in relation to a similar measurement in a reference medium, the dynamic range of the quantities used in the calculations is limited and the accuracy of the reconstructed image is enhanced. A further advantage consists in that light source and photodetectors need not be calibrated. Moreover, the use of normalized intensities also reduces effects in the reconstructed images which are due to the edges of the turbid medium. An example of the normalized intensity is given by the formule:

$$I'(m, n) = \ln\left(\frac{I_{measurement}(m, n)}{I_{calibration}(m, n)}\right),$$

in which $I_{measurement}(m,n)$ represents the measured intensity of light having traveled along a light path in a turbid medium between a measuring light source m and a measuring position n, and $I_{calibration}(m,n)$ represents a previously measured intensity of light having traveled along a light path in the reference medium between the measuring light source m and the measuring position n.

A next version of the method according to the invention is characterized in that the weighting factor is dependent on a combination of noise of the measurement, the measured intensity of the measurement, the noise of the reference intensity and the measured reference intensity.

It is a further object of the invention to provide a device yielding reconstructed images containing fewer artefacts. To this end, the device is characterized in that it includes means for determining a weighting factor which reduces the effect exerted on the reconstructed image by the measured intensities with a high noise factor in comparison with the effect exerted by the measured intensities with a low noise factor.

BRIEF DESCRIPTION OF THE DRAWINGS

The above and other, more detailed aspects of the invention will be described in detail hereinafter, by way of example, with reference to the drawing. Therein.

DETAILED DESCRIPTION OF THE PREFERRED EMBODIMENT

Figure 1:
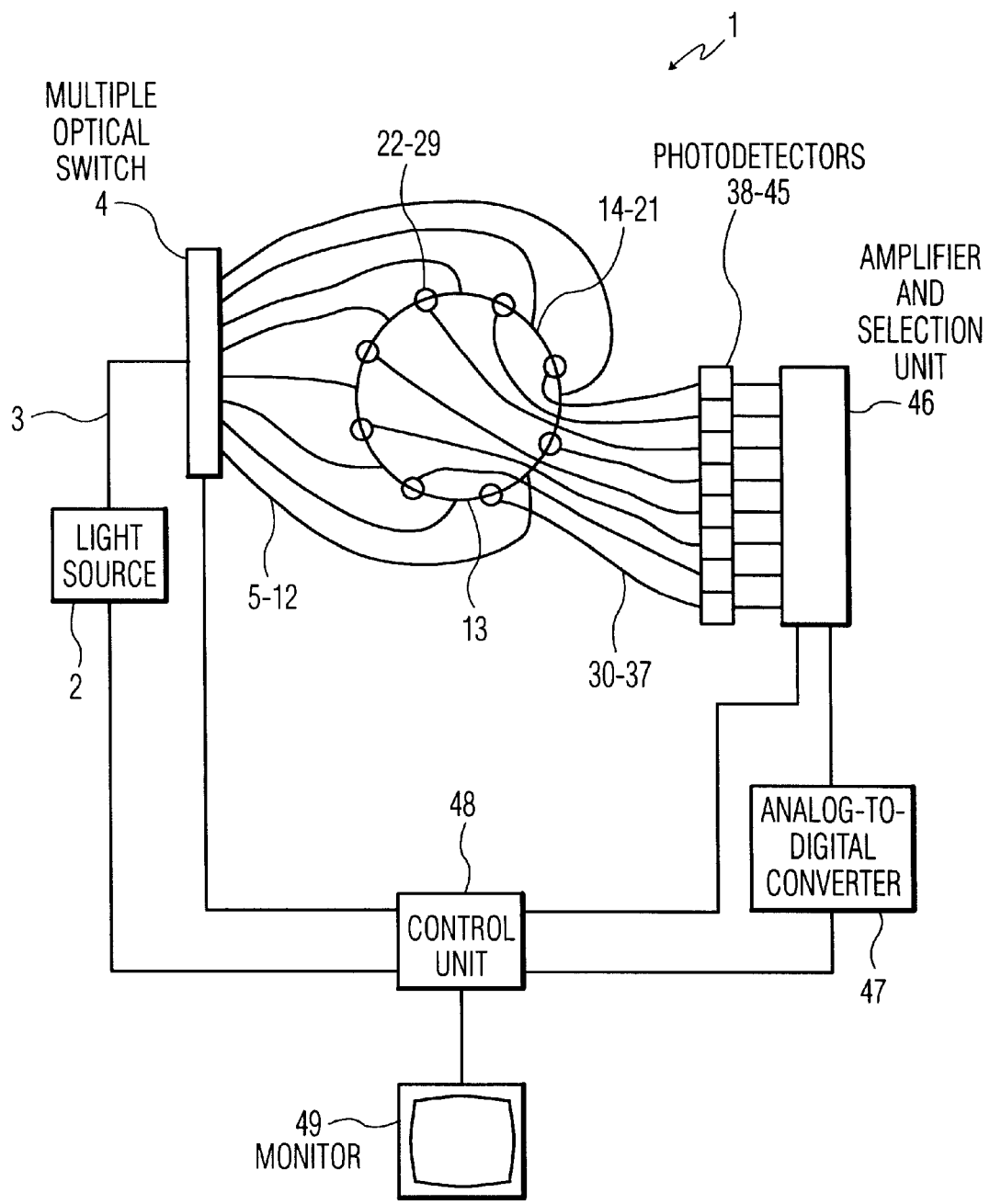
FIG. 1 shows a device for performing measurements on a turbid medium.

FIG. 1 shows an embodiment of a device according to the invention, this embodiment being an optical mammography device 1. Even though the device according to the invention is described by way of example, as a mammography device, it can also be used for the examination of other parts of a human or animal body. The device described herein is intended for the localization of inhomogeneities in in vivo breast tissue of a part of a breast of a human body. A malignant tumor is an example of such an inhomogeneity. The device according to the invention is arranged to image such anomalies when they are still very small, so that a carcinoma can be detected at an early stage. However, such detection takes place without exposing the patient to the risks of examination by means of ionizing radiation, for example X-rays.

In this embodiment, the device 1 includes a first plurality of M measuring light sources 14–21, a second plurality of N photodetectors 38–45, and a holder 13. The measuring light sources are mounted in the wall of a holder 13 in positions $r_m$, where m=1 ... M. The N photodetectors 38–45 are optically coupled to photodetector openings 22–29 in positions $r_n$ in the holder 13, where n=1 ... N. In other embodiments, the numbers M and N are fixed and lie, for example between 64 and 256. In practice these numbers equal 256 for M as well as N. The described device 1 is suitable for performing circular symmetrical intensity measurements. In FIG. 1 the number of measuring light sources 14–21 and the number of photodetector openings 22–29 are chosen to be 8 for the sake of simplicity. The device 1 also includes a light source 2, a first optical light conductor 3, a multiple optical switch 4 and a plurality of optical conductors 5–12. The multiple optical switch 4 connects the light source 2, via the first optical conductor 3 and a second optical conductor, to one of the light-transmitting openings 14–21 in the wall of the holder 13; these openings constitute the measuring light sources. The light source 2 used is, for example a semiconductor laser of a wavelength of 810 nm. The measuring device 1 also includes a third plurality of optical conductors 30–37, means for converting a signal of one of the photoconductors 38–45 in a digital value representing a measured intensity, comprising an amplifier and selection unit 46, an analog-to-digital converter 47. Furthermore the measuring device comprises a control unit 48. The third optical conductors 30–37 are connected, via the photodetector openings 22–29 in the wall of the holder 13, to the corresponding number of photodetectors 38–45. The outputs of the photodetectors 38–45 are connected, via the amplifier and selection unit 46, to the analog-to-digital converter 47. The output of the analog-to-digital converter is connected to an input of the control unit 48, for example a microcomputer. Subsequently, the control unit 48 reconstructs an image of the interior of the part of the breast to be imaged. A monitor 49 then displays the reconstructed image of the interior of the part of the breast to be imaged.

Figure 2:
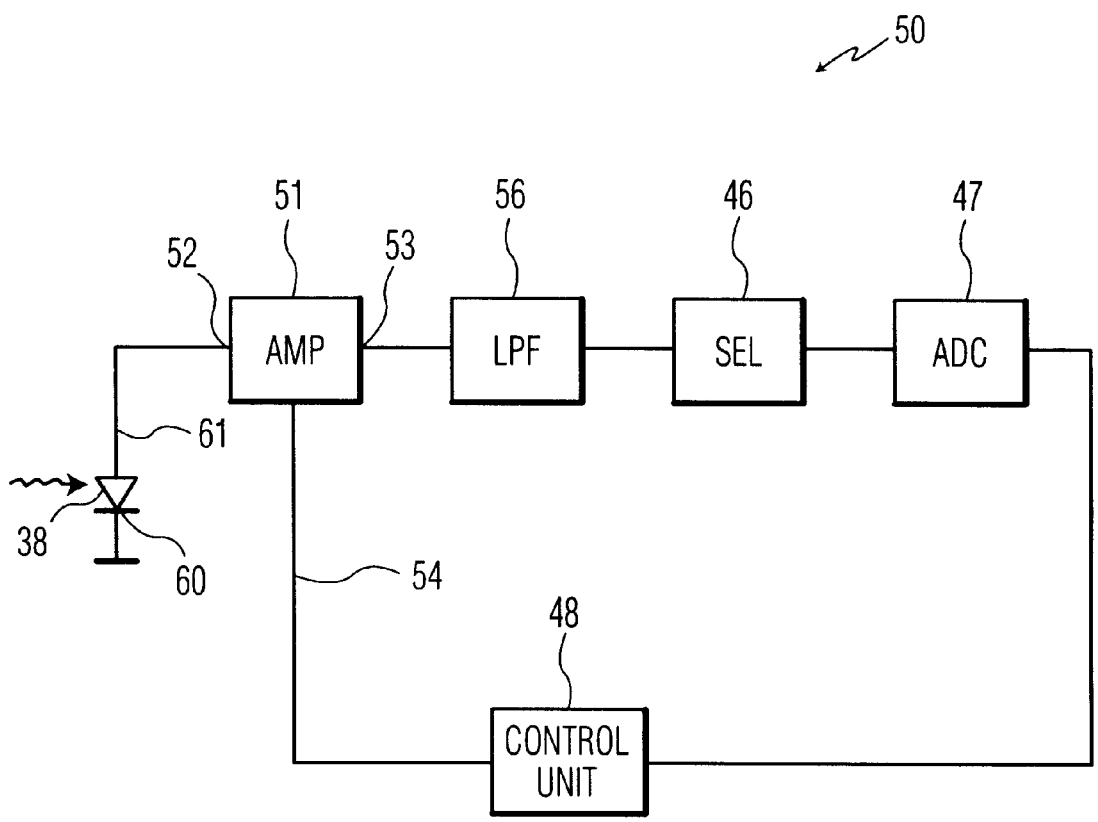
FIG. 2 shows a block diagram of a measuring chain.

FIG. 2 shows a block diagram 50 of a measuring chain. The measuring chain includes a photodiode 38, an amplifier 51, a low-pass filter 56, a selection unit 46 and an analog-to-digital converter 47. The amplifier 51 includes a transimpedance amplifier whose transfer factor can be switched, for example between four transfer factors of $2.2 \cdot 10^{11}$, $2.15 \cdot 10^9$, $2.12 \cdot 10^7$ and $2.07 \cdot 10^5$ volts per ampere. The transfer factor is adjusted, for example by means of a switching signal which is applied to a switching input 54 of the amplifier 51 by the control unit 48. Furthermore, an input 52 of the amplifier is connected to an anode 61 of the photodiode 38. A cathode 62 of the photodiode is connected to ground. The photodiode 38 is, for example of the type BPX63 marketed by Siemens. The output 53 of the amplifier is connected to an input of the analog-to-digital converter 47 via the low-pass filter 56 and the selection unit 46. A cut-off point of the low-pass filter lies, for example at 20 Hz. For example, the analog-to-digital converter 47 is a 16-bit type, for example an OITO 16XE-50 as marketed by National Instruments. The transfer factor of the amplifier is adjusted by the control unit 48 in such a manner that the value of a measured voltage at the output 53 of the amplifier 51 is maximum but not higher than the maximum permissible input voltage for the analog-to-digital converter 47. The maximum permissible input voltage for said type of analog-to-digital converter amounts to 10 volts.

In order to reconstruct an image of the interior of a part of the turbid medium, for example a part of the breast of a female, the part of the breast to be examined is immersed in a calibration medium in the holder 13 of the mammography device 1 during the execution of the intensity measurements. The calibration medium serves inter alia to couple the light from the measuring light sources into the breast tissue. An example of a calibration medium consists of a 1% Intralipid solution in water whose attenuation coefficient $\kappa_1$ corresponds to a predetermined mean attenuation coefficient of the breast tissue. Subsequently, the control unit 48 performs intensity measurements for each measuring light source photodetector pair (m,n), so that an intensity is measured between a measuring light source m and the photodetector n of the measuring light source photodetector pair (m,n). In the case of, for example 256 light sources and 256 photodetectors, the number of measurements amounts to $256^2$.

In order to limit the dynamic range of the numbers, use is preferably made of a normalized intensity in relation to an intensity of an analog measurement in a reference medium in conformity with $I^2 = \ln(I_{measurement}(m,n)) - \ln(I_{ref}(m,n))$, in which $I_{measurement}(m,n)$ represents a value of an intensity measurement of light transported through the breast tissue between the selected measuring light source m and the selected photodetector n, and $I_{ref}(m,n)$ represents a value of an intensity measurement of light transported through the reference medium between the selected measuring light source m and the selected photodetector n.

An example of a first version of the reconstruction method for reconstructing an image from the normalized intensities is formed by the known algebraic reconstruction method as disclosed in the cited article "The forward and inverse problems in time resolved infra-red imaging", published by S. R. Arridge, SPIE, IS11:35, 1993. According to the known method, an intensity is measured for a light source and a detector, after which the measured intensity is preferably normalized in relation to a reference medium in conformity with $y(i) = \ln(I_{measurement}) - \ln(I_{ref})$. Subsequently, a difference d(k) is determined between the normalized intensities Y(i) with a matrix product of a sensitivity matrix A(i,j) and a predetermined first image x(j), in which x(j) represents the variation of the attenuation coefficient $\Delta\kappa$ of a volume element j. Subsequently, the difference d(i) is normalized with, for example a factor $$\frac{1}{\sum_j (A(i,j))^2}$$

Subsequently, a next image is determined in conformity with:

$$x(j) = x(j) + \beta A^T(j,i) d(k)$$

in which
x(j) represents the first image, and
$A^T(j,i)d(k)$ represents the product of the transposed sensitivity matrix and the normalized difference d(k), and
β represents a convergence factor.

A matrix element (ij) of the sensitivity matrix A(ij) is determined by the sensitivity function $F(s(i),d(i),\kappa)$, in which the row number corresponds to a light source detector pair (m,n) of a measurement i, and the column number corresponds to a position p in space of a volume element j. The sensitivity factor function $F(s(i),d(i),\kappa)$ is determined by $$F(s(i), d(i), \kappa) = \frac{V\kappa_0}{2\pi} \frac{|s(i) - d(i)|}{|s(i) - p(j)| \times |p(j) - d(i)|} e^{-\kappa_0(|s(i) - p(j)| + |p(j) - d(i)| - |s(i) - d(i)|)} \quad (1)$$

in which
V represents the volume of a volume element j in the turbid medium,
s(i)–d(i) represents a distance between a light source(m) in a position s(i) and a detector m in a measuring position d(i) for a measurement (i), s(i)–p(j) represents a distance between the position s(i) of the light source m during the measurement (i) and the position p(o) of a volume element (j) for which the variation of the attenuation coefficient κ is determined, p(j)–d(i) represents the distance between the position p(j) of said volume element j and the measuring position d(i) of the detector m during the measurement (i), and F(s(i),d(i),κ) represents the relative variation of the measured intensity in a position d(i) of a light source m in the position s(i).

The number of elements of the vector x(j) amounts to, for example $64 \times 64 \times 64 = 2^{18}$. The foregoing steps are repeated for all measurements i=1 to M×N light source and measuring positions, the first image being replaced after an iteration step by the next image thus calculated.

In order to avoid artefacts in the reconstructed image which are due to a poor signal-to-noise ratio in the normalized intensity, the convergence factor β is preferably chosen to be equal to the weighting factor W which is dependent on a reciprocal value of the noise factor.

When use is made of a simple noise model, in which the noise of individual sources of the measuring chain is not correlated, the noise factor can be determined by forming the root mean square sum of the individual components of the measuring chain from the photodiode up to and including the analog-to-digital converter. The noise factor contains contributions, for example from the noise in the photocurrent generated in the photodiode, the conversion noise of the analog-to-digital converter and errors due to, for example different transfer factors of the amplifier. If the normalized measured intensity is determined, for example as $I' = \ln(I_{data} - I_{dark,dark}) - \ln(I_{ref} - I_{dark,ref})$, the error σ of the individual components is determined as $I_{noise}/(I_{data} - I_{dark,data})$.

The weighting factor of an actual measurement i is then determined by:

$$W_i = 1/\sigma = \frac{1}{\sqrt{\sum_n (\sigma_n)^2}} \quad (2)$$

The total noise is subsequently determined by $$\sigma^2 = (C_1)^2 + (C_2)^2 + (\sigma_{1,data})^2 + (\sigma_{2,data})^2 + (\sigma_{1,ref})^2 + (\sigma_{2,ref})^2$$

in which $C_1$ represents a normalization constant, and
$C_2$ represents an amplifier factor noise.

Furthermore, $\sigma_{1,data}$ is determined by $$\frac{N_{det,data}}{(I_{data} - I_{dark,data})}$$

in which $N_{det,data}$ represents the detector noise during the actual measurement, $I_{data}$ represents the measured photocurrent, and $I_{dark,data}$ represents the measured dark current of the photodetector during the actual measurement $\sigma_{2,data}$ is determined by $$\frac{N_{det,ref}}{(I_{ref} - I_{dark,ref})}$$

in which $N_{ADC}$ represents the conversion noise upon conversion of analog into digital signals for the actual measurement.

$\sigma_{1,ref}$ is determined by $$\frac{N_{det,ref}}{(I_{ref} - I_{dark,ref})}$$

in which $N_{det,ref}$ represents the detector noise during the reference measurement, $I_{ref}$ represents the photocurrent measured during the reference measurement, $I_{dark,ref}$ represents the measured dark current of the photodetector during the reference measurement.

$\sigma_{2,ref}$ is determined by $$\frac{N_{ADC,ref}}{(I_{ref} - I_{dark,ref})}$$

in which $N_{ADC}$ represents the conversion noise during the conversion of analog-to-digital signals for the reference measurement.

The constant $C_1$ ensures that the weighting factor $W_i$ can assume a value of no more than 1 and it indicates the degree of reproducibility of the measurement and amounts to, for example 0.001.

The constant $C_2$, representing the amplifier factor noise, is taken into account only if the measured values of the photocurrents of the actual measurement and the reference measurement, respectively, have been measured for different ranges of the amplifier circuit 51. The value of the constant $C_2$ amounts to, for example 0.03.

The magnitude of the conversion noise of the analog-to-digital converter $N_{ADC}$ is determined from the number of bits representing the converted digital value and the maximum voltage difference at the input. The present example utilizes a 16-bit value and the maximum voltage difference at the input amounts to, for example 10 V. The conversion noise then amounts to $$10/65653 = \frac{1}{\sqrt{K}} \text{ Volts,}$$

in which K represents the number of measurements performed per light source-detector pair (i,j).

The noise in the photocurrent for the actual measurement and the reference measurement is estimated from the root mean square differences between the measured photocurrent and the is measured dark current, given by $$(N_{ref}^{det})^2 = \frac{1}{2N} \sum_{det'=1}^{N} \left(I_{dark,data}^{det'} - I_{dark,ref}^{det'}\right)^2 + \frac{1}{2}(I_{dark,data}^{det} - I_{dark,data}^{det})^2 + C_3,$$

in which N represents the number of detectors, and $C_3$ represents a constant.

The constant $C_3$ is dependent on the Poisson noise of the photodetector used to measure the photocurrent and the amplifier circuit 39. The value of $C_3$ amounts to, for example 0.1 times the value of the dark current which amounts to, for example approximately 10 femto ampere. Summing is performed over all N photodetectors present. If the value of a measurement of the photocurrent $I_{data}$ is smaller than the dark current $I_{dark}$, by way of exception the measurement is not taken into account for the reconstruction.

An example of a second version of a reconstruction method includes a step which comprises a back-transformation. This version utilizes a weighting factor in order to reduce an effect exerted on the reconstructed image by the normalized intensities with a high noise factor in relation to the effect exerted by the normalized intensities with a low noise factor. This second version includes a further step in which variations are determined of the attenuation coefficients associated with the measured intensities of the various light paths, where $$\Delta\kappa(i) = \frac{y(i)}{|s(i) - d(i)|},$$

in which $\Delta\kappa(i)$ represents the measured variation of the attenuation coefficient of a light source detector pair (m,n) of a measurement i, y(i) represents the normalized intensity, and $|s(i)-d(i)|$ represents the distance between a measuring light source n in the position s(i) and a photodetector m in the position d(i) associated with the measurement i.

Subsequently, during a next step an image is reconstructed by means of back-transformation which includes a weighted mean value of a transposed sensitivity matrix with the variation determined in the attenuation coefficient of the light paths.

$$x(j) = \frac{\sum_{i=0}^{i=N\times M} A^T(j,i)\Delta\kappa(i)}{\sum_{i=0}^{i=N\times M} A^T(j,i)}$$

in which x(j) represents the variation of the attenuation coefficient $\Delta\kappa$ of a volume element j, $A^T(j,i)$ represents the transposed sensitivity matrix A(ij), $\Delta\kappa(i)$ represents the measured variation of the attenuation coefficient of a light source detector pair (m,n) of a measurement i, and the product N×M represents the number of measurements.

In order to avoid artefacts in the reconstructed image which are due to a poor signal-to-noise ratio, the elements of the transposed sensitivity matrix are weighted by the weighting factor determined in conformity with the formula (2). The back-transformation is performed as $$x(j) = \frac{\sum_{i=0}^{i=N\times M} A^T(j,i)W_i\Delta\kappa(i)}{\sum_{i=0}^{i=N\times M} A^T(j,i)W_i}$$

in which x(j) represents the variation of the attenuation coefficient $\Delta\kappa$ of a volume element j, $A^T(j,i)$ represents the transposed sensitivity matrix, $\Delta\kappa(i)$ represents the measured variation of the attenuation coefficient associated with an intensity y(i) of a measurement i during which a light source is present in a position s(i) and a photodetector is present in a position d(i), the product N×M represents the number of measurements, and $W_i$ represents the weighting factor of a measurement i.

The sensitivity matrix may also be chosen, for example, in such a manner that the back-transformation includes a back-projection. The sensitivity matrix then comprises first elements which are equal to zero and second elements which are not equal to zero; volume elements corresponding to the second elements are then situated on a line between the measuring light source m in the position s(i) a photodetector in the position d(i) in the turbid medium p(i). furthermore, such second elements have a constant value which is equal to, for example 1. Reconstruction by back-projection is known per se from the handbook "Fundamentals of Image Processing" by A. K. Jain et al., Prentice hall, 1989, pp. 439–441.

All references cited herein, as well as the priority document European Patent Application 98202109.9 filed Jun. 25, 1998, are incorporated herein by reference in their entirety and for all purposes to the same extent as if each individual publication or patent or patent application was specifically and individually indicated to be incorporated by references in its entirety for all purposes.

What is claimed is:

1. A method of localizing an object in a turbid medium comprising:

irradiating the turbid medium with light, measuring intensities of a part of the light transported through the turbid medium along a plurality of light paths from a source point where the light enters the turbid medium to a measuring point where the light leaves the turbid medium, and reconstructing an image of the interior of the turbid medium from a combination of measured intensities, wherein a weighting factor is applied to the combination of measured intensities which reduces an effect exerted on the reconstructed image by the measured intensities with a high noise factor relative to the effect exerted thereon by the measured intensities with a low noise factor, wherein, for a light source and a measuring position at which intensities are measured, the method further comprises:

determining an estimated intensity from a transformation of a predetermined first image, determining a difference between the measured intensities and the estimated intensity, and determining a next image from the first image, a convergence factor and a back-transformation of the difference, the convergence factor being chosen depending on the weighting factor.

2. A method as claimed in claim 1, in which the transformation contains a product of a sensitivity matrix and the first image.

3. A method as claimed in claim 1, in which the back-transformation contains a product of an estimate of an inverse sensitivity matrix and the difference between the measured intensities and the calculated intensities.

4. A method of localizing an object in a turbid medium comprising:

irradiating the turbid medium with light, measuring intensities of a part of the light transported through the turbid medium along a plurality of light paths from a source point where the light enters the turbid medium to a measuring point where the light leaves the turbid medium, and reconstructing an image of the interior of the turbid medium from a combination of measured intensities, wherein a weighting factor is applied to the combination of measured intensities which reduces an effect exerted on the reconstructed image by the measured intensities with a high noise factor relative to the effect exerted thereon by the measured intensities with a low noise factor, wherein the method further comprises:

determining variations of attenuation coefficients of the light paths from the measured intensities, and determining a variation of an attenuation coefficient of a volume element of the turbid medium by means of a back-transformation which contains a weighted mean value of an estimate of an inverse sensitivity matrix with the variations determined for the attenuation coefficients of the light paths, the effect of the noise factor on the reconstruction being determined by the product of the weighting factor and the elements of the estimate of the inverse sensitivity matrix.

5. A method of localizing an object in a turbid medium comprising:

irradiating the turbid medium with light, measuring intensities of a part of the light transported through the turbid medium along a plurality of light paths from a source point where the light enters the turbid medium to a measuring point where the light leaves the turbid medium, and reconstructing an image of the interior of the turbid medium from a combination of measured intensities, wherein a weighting factor is applied to the combination of measured intensities which reduces an effect exerted on the reconstructed image by the measured intensities with a high noise factor relative to the effect exerted thereon by the measured intensities with a low noise factor, wherein the method further comprises correcting the measured intensities by way of a normalized intensity which is determined by a combination of the measured intensity associated with a light path and a measured reference intensity associated with the light path in a reference medium.

6. A method of localizing an object in a turbid medium comprising:

irradiating the turbid medium with light, measuring intensities of a part of the light transported through the turbid medium along a plurality of light paths from a source point where the light enters the turbid medium to a measuring point where the light leaves the turbid medium, and reconstructing an image of the interior of the turbid medium from a combination of measured intensities, wherein a weighting factor is applied to the combination of measured intensities which reduces an effect exerted on the reconstructed image by the measured intensities with a high noise factor relative to the effect exerted thereon by the measured intensities with a low noise factor, wherein the weighting factor is dependent on a reciprocal value of a noise factor, wherein the method further comprises determining the noise factor by a combination of noise of the measurement, the measured intensity of the measurement, the noise of the reference intensity and the measured reference intensity.

\* \* \* \* \*